United States Patent
Moses et al.

(10) Patent No.: US 7,869,863 B2
(45) Date of Patent: Jan. 11, 2011

(54) APPARATUS AND METHOD FOR NON-INVASIVE, PASSIVE FETAL HEART MONITORING

(75) Inventors: Edward J. Moses, Rockville, MD (US); John A. Cristion, Columbia, MD (US); Susanne M. Daniels, Ann Arbor, MI (US); Wayne I. Sternberger, Highland, MD (US); Timothy P. Magnani, Fulton, MD (US)

(73) Assignee: The Johns Hopkins University, Baltimore, MD (US)

( * ) Notice: Subject to any disclaimer, the term of this patent is extended or adjusted under 35 U.S.C. 154(b) by 431 days.

(21) Appl. No.: 11/971,940

(22) Filed: Jan. 10, 2008

(65) Prior Publication Data

US 2009/0182242 A1 Jul. 16, 2009

(51) Int. Cl.
*A61B 5/04* (2006.01)
(52) U.S. Cl. .................................... 600/511
(58) Field of Classification Search ............... 600/511, 600/338, 376, 521
See application file for complete search history.

(56) References Cited

U.S. PATENT DOCUMENTS

| | | | |
|---|---|---|---|
| 3,703,168 A | 11/1972 | Frink | |
| 4,211,237 A | 7/1980 | Nagel | |
| 4,573,479 A | 3/1986 | Tuccillo | |
| 4,781,200 A | 11/1988 | Baker | |
| 4,945,917 A | 8/1990 | Akselrod et al. | |
| 4,951,680 A | 8/1990 | Kirk et al. | |
| 4,961,428 A | 10/1990 | Nikias | |
| 4,974,598 A | 12/1990 | John | |
| 5,042,499 A | 8/1991 | Frank et al. | |
| 5,372,139 A | 12/1994 | Holls et al. | |
| 5,469,856 A | 11/1995 | Lundstrom et al. | |
| 5,596,993 A | 1/1997 | Oriol et al. | |
| 5,630,425 A | 5/1997 | Panescu et al. | |
| 5,687,737 A | 11/1997 | Branham et al. | |
| 5,704,365 A | 1/1998 | Albrecht et al. | |
| 5,706,402 A | 1/1998 | Bell | |
| 5,795,303 A | 8/1998 | Swanson et al. | |
| 6,658,284 B1 | 12/2003 | Rosen et al. | |
| 6,751,498 B1 * | 6/2004 | Greenberg et al. | 600/511 |
| 6,978,169 B1 | 12/2005 | Guerra | |
| 2004/0243015 A1 * | 12/2004 | Smith et al. | 600/511 |
| 2005/0010120 A1 | 1/2005 | Jung et al. | |
| 2005/0267376 A1 | 12/2005 | Marossero et al. | |
| 2005/0267377 A1 | 12/2005 | Marossero et al. | |
| 2007/0027396 A1 | 2/2007 | Assaleh et al. | |
| 2007/0270704 A1 * | 11/2007 | Ghanem et al. | 600/521 |

* cited by examiner

*Primary Examiner*—Carl H Layno
*Assistant Examiner*—Brian T Gedeon
(74) *Attorney, Agent, or Firm*—Francis A. Cooch (57) ABSTRACT

The present invention provides a method and apparatus for monitoring the fetal condition in an objective, quantitative, and non-invasive manner by enabling continuous and highly specific data collection during pre-natal development and the intra-partum period. In an embodiment, monitoring the fetal condition comprises monitoring a fetal heart rate, a fetal heart rate variability, and/or the fetal heart vector orientation of a fetus in a pregnant mother. Automated signal processing techniques are applied to a multiplicity of transducers to select an optimum signal vector to monitor at least one of a fetal heart rate, a fetal heart rate variability, and/or the fetal heart vector orientation of a fetus in a pregnant mother.

22 Claims, 11 Drawing Sheets

STTR Montage for FHM

- 1+: T RA
- 2+: T LA
- 3+: T V3
- 4+: T V1
- 5+: T V5
- 6+: A V3
- 7+: A V1
- 8+: A V5
- 9+: A V2
- 10+: A V6
- 16+: A V4
- 16-: A TBD
- Pt Gnd: T RL

*FIG. 4e*

- Chan 1: 1 – 2
- Chan 2: 1 – 5
- Chan 3: 2 – 5
- Chan 4: 2 – 3
- Chan 5: 2 – 4
- Chan 6: 1 – 3
- Chan 7: 1 – 4
- Chan 8: 7 – 8
- Chan 9: 4 – 8
- Chan 10: 5 – 8
- Chan 11: 5 – 9
- Chan 12: 16
- Chan 13: 4 – 10
- Chan 14: 4 – 7
- Chan 15: 6 – 7
- Chan 16: 6 – 8

APPARATUS AND METHOD FOR NON-INVASIVE, PASSIVE FETAL HEART MONITORING

STATEMENT OF GOVERNMENTAL INTEREST

This invention was made with Government support under National Institute of Health/NHLBI grant 1R41 HL079790-01.

CROSS REFERENCE TO RELATED APPLICATIONS

This application is related to U.S. provisional applications: Ser. No. 60/850,788, filed on Oct. 11, 2006; and Ser. No. 60/850,786 filed on Oct. 11, 2006, each of which is incorporated herein by reference in its entirety.

BACKGROUND OF THE INVENTION

1. Field of the Invention

The invention relates generally to biomedical devices and, in particular, the invention relates to the accurate noninvasive measurement of instantaneous fetal heart rate.

2. Description of the Related Art

Significant progress has been made in the science of electrocardiography since 1938. Heart rate and biophysical profiles are routinely derived from multi-lead electrocardiograms (ECGs) in animals and humans after birth. In contrast, only limited heart monitoring technologies exist for the fetus. Moreover, available technology fails to satisfy many existing needs in fetal ECG monitoring, both to support clinical assessment of fetal health and fundamental research on fetal development.

The present inventors have determined that there is a significant need to reduce the technology gap that persists in fetal ECG monitoring in order to support advanced assessments of fetal health and development.

SUMMARY OF THE INVENTION

Therefore, the present invention has been made in view of the above problems. Accordingly, the present invention provides a method and apparatus for monitoring the fetal condition in an objective, quantitative, and non-invasive manner by enabling continuous and highly specific data collection during pre-natal development and the intra-partum period. This monitoring will aid in the fetal and maternal treatment planning regimen potentially earlier than presently feasible, thus facilitating or indicating interventions which may reduce maternal and fetal morbidity and mortality. In an embodiment, monitoring the fetal condition comprises monitoring a fetal heart rate, a fetal heart rate variability, and/or the fetal heart vector orientation of a fetus in a pregnant mother.

According to one aspect of the invention, automated signal processing techniques are applied to a multiplicity of transducers to select an optimum signal vector to monitor at least one of a fetal heart rate, a fetal heart rate variability, and/or the fetal heart vector orientation of a fetus in a pregnant mother.

According to another aspect of the invention, a fully automated apparatus is disclosed, requiring no user intervention, for monitoring at least one of a fetal heart rate, a fetal heart rate variability, and/or the fetal heart vector orientation of a fetus in a pregnant mother. In one embodiment, the apparatus comprises a multiplicity of transducers, means for acquiring unipolar EKG signals collected by the multiplicity of transducers and means for creating accurate bipolar vectors from the unipolar EKG signals. The apparatus further comprises a data collection interface including automated and optimized signal processing parameter controls which eliminate a requirement for certain operator decisions ("man-in-the-loop") during processing. The data collection interface of the invention provides numerous advantages over prior art data collection interfaces including, for example, fewer electrodes, preserved signal to noise and greater adaptability to accommodate pregnant women of different sizes, shapes and gestational age.

Other advantages provided by the invention, include maximizing the health and well-being of the mother and fetus by reducing unnecessary or ineffective interventions (e.g., unnecessary C-sections) and the number of babies born with effects of such interventions, and supporting fetal development research.

BRIEF DESCRIPTION OF THE DRAWINGS

These and other objects, features and advantages of the invention will be apparent from a consideration of the following Detailed Description Of The Invention considered in conjunction with the drawing Figures, in which.

DETAILED DESCRIPTION OF THE PREFERRED EMBODIMENTS

In the following discussion, numerous specific details are set forth to provide a thorough understanding of the present invention. However, those skilled in the art will appreciate that the present invention may be practiced without such specific details. In other instances, well-known elements have been illustrated in schematic or block diagram form in order not to obscure the present invention in unnecessary detail.

It is further noted that, unless indicated otherwise, all functions described herein may be performed in either hardware or software, or some combination thereof. In a preferred embodiment, however, the functions are performed by a processor, such as a computer or an electronic data processor, in accordance with code, such as computer program code, software, and/or integrated circuits that are coded to perform such functions, unless indicated otherwise.

It should be appreciated that the present invention can be implemented in numerous ways, including as a process, an apparatus, a system, a device, a method, or a computer readable medium such as a computer readable storage medium or a computer network where program instructions are sent over optical or electronic communication links. Several inventive embodiments of the present invention are described below.

Overview

In accordance with the present invention, there are provided herein methods and systems for monitoring the EKG, heart rate and heart rate variability in an in utero fetus. The invention provides capabilities for fully automating the monitoring process. In the described embodiments, fetal monitor algorithms are utilized which are controlled by a number of parameters that determine the sensitivity of the algorithms and the accuracy and rapidity with which they converge to estimates of interest. Parameters are generally classified as fixed or adjustable. Parameter values are determined based on input data characteristics and a pre-defined set of rules. The quality of a fetal waveform is evaluated based on a set of metrics (defined below). A feedback loop is employed which utilizes a quality score associated with the quality of the fetal waveform, based on one or more metrics, and dynamically adjusts appropriate parameters to ensure that the quality of the fetal waveform is optimized. Accordingly, there is disclosed automated means for extracting a high quality fetal signal from an abundance of abdominal channels, means for ascribing a data quality metric to the extracted fetal signal and means for adjusting parameters to maintain the highest quality fetal signal.

System Data Flow—Prior Art

Figure 1:
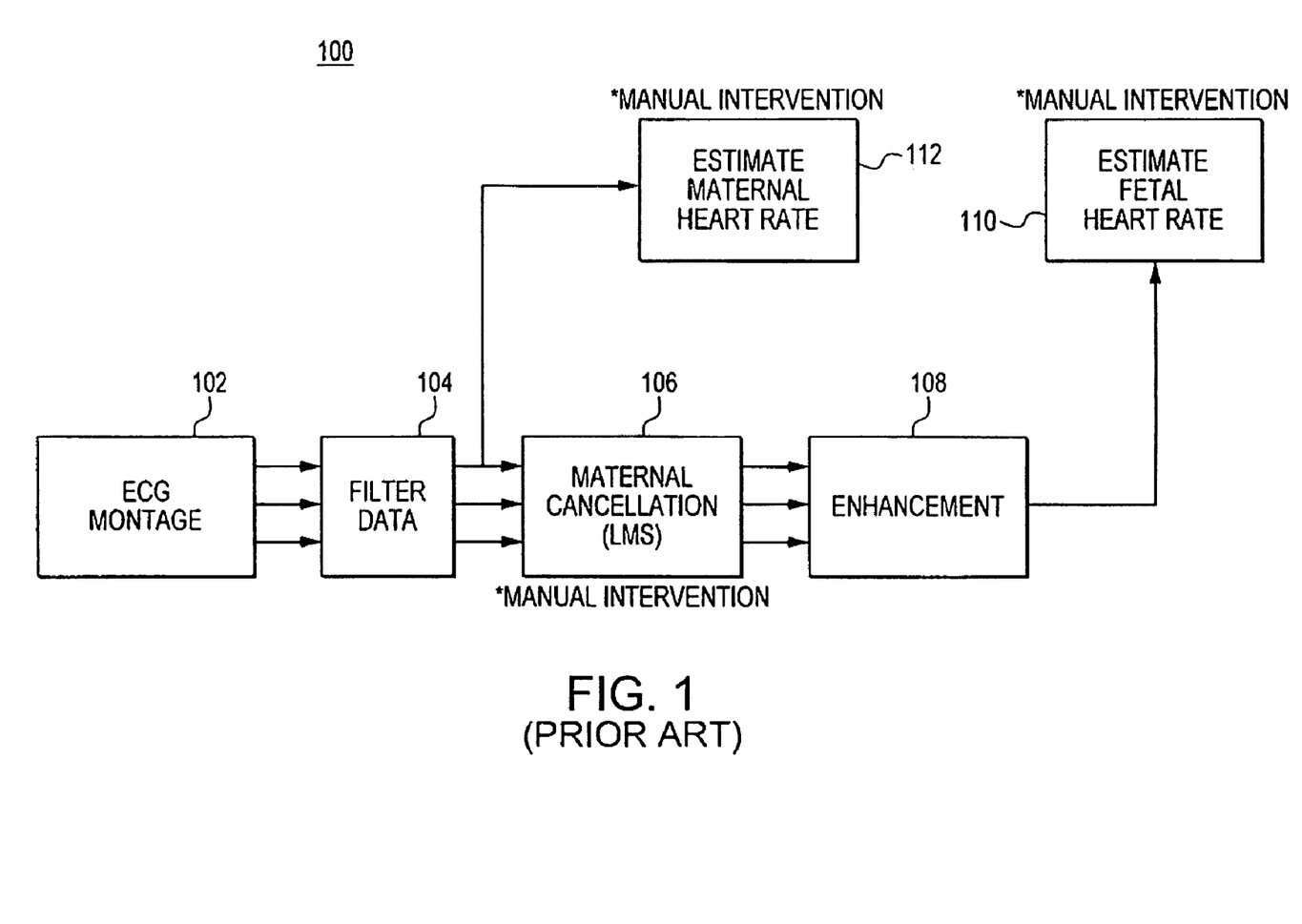
FIG. 1 is a block diagram of a system data flow, according to the prior art.

With reference now to FIG. 1, there is shown and described a block diagram of a system data flow 100, according to the prior art. The data flow begins with fetal ECG data collected by an electro-cardio-gram (ECG) montage 102. This data are provided to a filter stage 104, defined by a pre-determined filter cut-off frequency and order. In some embodiments, the filter stage 104 can be a low-pass filter, a high-pass filter, or a combination. The filtered output data are provided to a maternal cancellation stage 106. In the maternal cancellation stage 106, an operator must decide the appropriate adaptation rate for the LMS algorithm. As discussed more fully in U.S. Pat. No. 6,751,498, entitled "Apparatus and method for non-invasive, passive fetal heart monitoring", incorporated by reference herein in its entirety, in the maternal cancellation stage a weighted subset of the available signal channels (the "maternal" channels) are combined to provide an estimate of the maternal ECG. This estimate is subtracted from the remaining channels (the "fetal" channels) to approximately cancel the maternal signal on those channels. The weighting coefficients for the maternal channels are separately chosen for each fetal channel and temporally adapt so as to continuously minimize the residual mean square signal on each fetal channel." The maternal cancellation stage 106 is defined by the operator selected adaptation rate for a least-mean-square (LMS) algorithm. In some embodiments, the maternal cancellation stage 106 is followed by an enhancement stage 108.

In some embodiments, an "enhanced" fetal signal is generated that is an appropriate linear combination of the available fetal channels. Alternatively the operator can select the "best" of the available fetal channels for further processing."

For those embodiments that utilize an enhancement stage 108, an operator is required to manually select an optimal set of processing channels to evaluate.

Lastly, estimations of both the fetal and maternal and fetal heart rates are derived via a correlation method, as shown at 110 and 112, respectively, requiring the user to select timing intervals to place limits on the anticipated maternal and fetal heart rates. The correlation method estimates heart rate by auto correlating an ECG signal with itself. The autocorrelation function of a periodic signal will typically have a strong peak at the lag corresponding to the signal period; establishing the position of this peak determines the period. However, this method is not ideal for two reasons. First, the autocorrelation function typically also has peaks at integer multiples of the signal period. The multiple peaks can lead to ambiguities in the estimate. Untangling the ambiguities often requires placing a priori limits on the expected signal period, which is undesirable. Second, this method intrinsically provides a time averaged estimate of the period; physicians prefer local measures of RR peak separation. The methods described herein eliminate both these objections.

As described above and illustrated in FIG. 1 in accordance with a prior art data flow configuration, the number of parameter choices and channel selections required of an operator is non-trivial.

As will become apparent, the present invention eliminates the requirement for certain operator decisions via both, automated and optimized signal processing parameter controls during processing and a robust and clinically acceptable data collection interface to the patient by optimizing the data collection hardware configuration.

System Data Flow

First Embodiment

Figure 2:
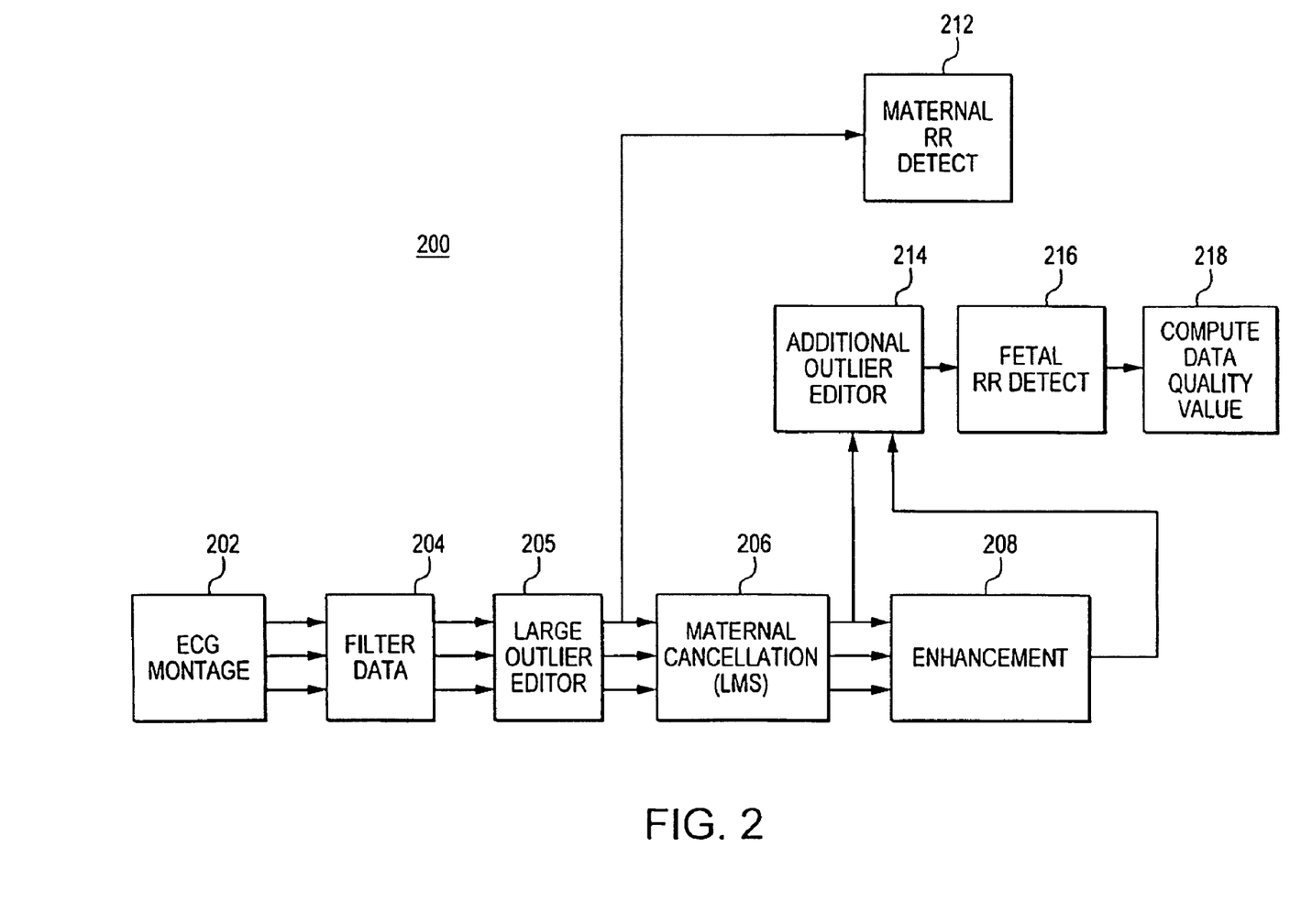
FIG. 2 is a block diagram of a system data flow, according to an embodiment of the invention.

With reference now to FIG. 2, there is shown and described a block diagram of a system data flow 200, according to an embodiment of the invention.

System data flow 200 represents an advance over the system data flow 100 of FIG. 1 in that it incorporates quantitative metrics to monitor the quality of the fetal ECG data at the various processing stages. The metrics are derived from measurements of the fetal ECG (e.g., variation of timing in the R-wave peaks), described further below.

Some elements of the system data flow 200 are similar to respective elements of the system data flow 100 illustrated in FIG. 1. That is, the data flow 200 includes an ECC montage 102, a data filter 104, a maternal cancellation stage 106, and an enhancement stage 108.

In addition to these known elements from the system data flow 100 of FIG. 1, to facilitate the incorporation of quantitative metrics to monitor the quality of the fetal ECG data, additional processing stages are incorporated into the processing flow. In one embodiment, these additional processing stages include a large outlier editor 205, an additional outlier editor 214, both of which are introduced to remove large transients from the data and improve the overall data quality. The final processing stage consists of a fetal RR detector 216 that identifies the timing of the fetal R-waves and a Compute data quality value module 218 for aggregating various computational metrics into an overall value used to quantitatively assess the validity of the data (i.e. based on data quality value can determine whether a given data channel is providing reliable data or not). In accordance with the operation of the data quality value module 218, statistical "clustering" techniques are used to divide the channels into "good" channels and "bad" channels, and a vector of centroid values is separately computed for the good channels and the bad channels. When new data is to be evaluated, the same set of metrics is computed for each fetal channel, and a quality measure developed that is the difference in "distance" of the new channel's metric vector from the good and bad centroid vectors. Channels lying relatively closer to the "good" centroid are judged to be of higher quality."

Second Embodiment

Figure 3:
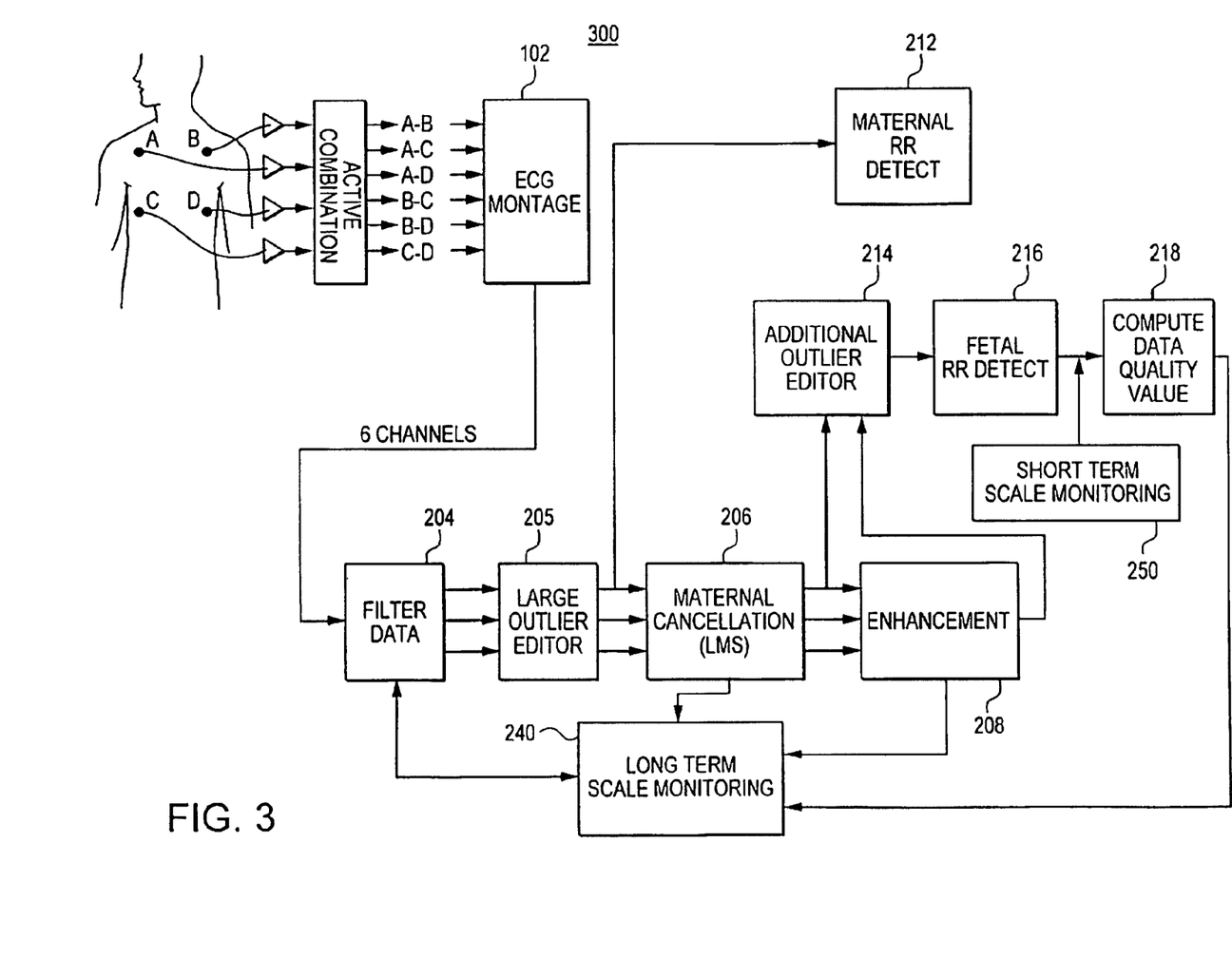
FIG. 3 is a block diagram of a system data flow, according to an embodiment of the invention.

With reference now to FIG. 3, there is shown and described a block diagram of a system 300, according to another embodiment of the invention. The system 300 is distinguishable from the previously described embodiment in that the presently described system 300 in addition to incorporating quantitative metrics to monitor the quality of the fetal ECG data, the present embodiment further includes a control feedback layer which serves to monitor the processing results at defined time intervals. The present embodiment further provides capabilities for dynamically forming signal vectors (i.e., input channels) by means of unipolar data acquisition to maximize the number of high quality input channels with a minimum of hardware.

In the present embodiment, processing results are autonomously monitored on both a short time-scale 250, on the order of 10 to 30 seconds and a long time-scale 240, on the order of 1 to 2 minutes. The short time-scale monitors one channel of the fetal ECG data and ensures that a reasonable fetal heart rate is being measured. The long time-scale monitors a set of ECG data channels and processing parameters to ensure that the final fetal ECG is optimal. The short time-scale is selected as an interval over which to address whether the fetal heart rate is present and is within physiologically acceptable bounds. The long time-scale is defined as an interval over which the system re-evaluates whether the fetal heart vector has moved within the monitoring montage array. It is understood that the durations for the two time-scales can be arbitrarily changed; the ranges of 10 to 30 seconds and 1 to 2 minutes were selected by way of example, and not limitation. At the chosen intervals, the results of the enhancement process are evaluated via metric and clustering approaches, to be described below, in addition to computing waveform quality scores heart rates.

In the case where the either the short term or long term monitoring results in an aberrant condition, in one embodiment, automated adaptive controls assess whether a signal processing anomaly exists or whether the aberrant condition is attributable to a clinical issue. In the former case where it is determined that a signal processing anomaly exists, the system re-assesses whether a new reference channel needs to be selected. In the latter case, where it is determined that a clinical issue exists, an alarm is provided to an attendant clinician.

With continued reference to FIG. 3, system data flow 300 may be described, in one aspect, as a concurrent process, capable of running during data collection and using data collected in near-real-time. It includes feedback loops where automated monitoring and control capabilities will execute, as will be described. Further, system 300 provides automated monitor capabilities that operate in tandem with an enhancement process. The two processes overlap to the extent that the monitoring and control processes assess the performance of the enhancement process to make changes to the enhancement process control parameters, and to use the output of the enhancement process to compute: fetal heart rate, maternal heart rate, and the fetal waveform quality score. These processes are described in greater detail as follows.

The apparatus of the present invention, according to the presently described embodiment, includes electrodes and signal processing circuitry to carry out the functionality described above.

The invention preferably starts with extracting, in real time, maternal and fetal vital signs using ECG electrodes that do not endanger fetal health. A set of ECG electrodes are preferably used to sense maternal-fetal vital signs.

Figure 4A:
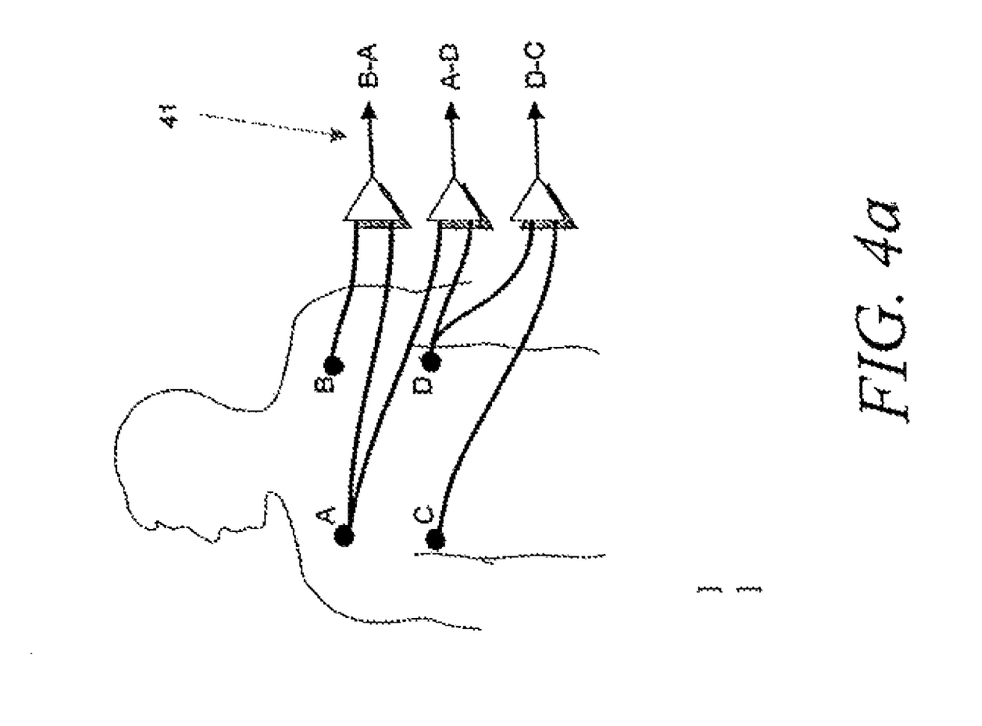
FIG. 4a illustrates a data collection interface employing a plurality of ECG amplifiers configured in a differential input mode using passive combination for acquiring a set of independent channels.

Referring now to FIG. 4a, to acquire a set of independent channels, a set of ECG leads or vectors connect to individual differential (bipolar) amplifiers. For example, ECG leads (vectors) labeled "A" and "B" in FIG. 4a are differentially coupled to a single differential (bipolar) amplifier 41. Differential (bipolar) amplifiers are used to maximize common mode rejection in the presence of noise. Acquisition systems based on differential inputs are well known. For example, a research-grade biomedical data acquisition system from Biopac Systems, Inc., Goleta, Calif., provides such a data acquisition system based on differential inputs.

In accordance with the configuration of FIG. 4a, the plurality of ECG amplifiers are configured in a differential input mode using passive combination. A passive impedance matching network (not shown) provides the one-electrode-to-multiple-amplifier breakout that is required to form the raw input signals. One drawback of using a differential input mode data acquisition system, such as the one shown in FIG. 4a, is a restriction on the number of input channels that can be collected. For example, the MP100 data acquisition system from Biopac Systems has an upper limit of 16 ECG channels that can be operated in unison. Other limitations of these types of systems include, for example, a limited number of input signals resulting from a limit on the number of channels, the orientation of the signal vectors is predefined by the placement of the electrodes, and a passive matching network having an exhibited susceptibility to noise. To overcome these limitations, the inventors contemplate the use of a more robust data collection interface, described as follows.

Figure 4B:
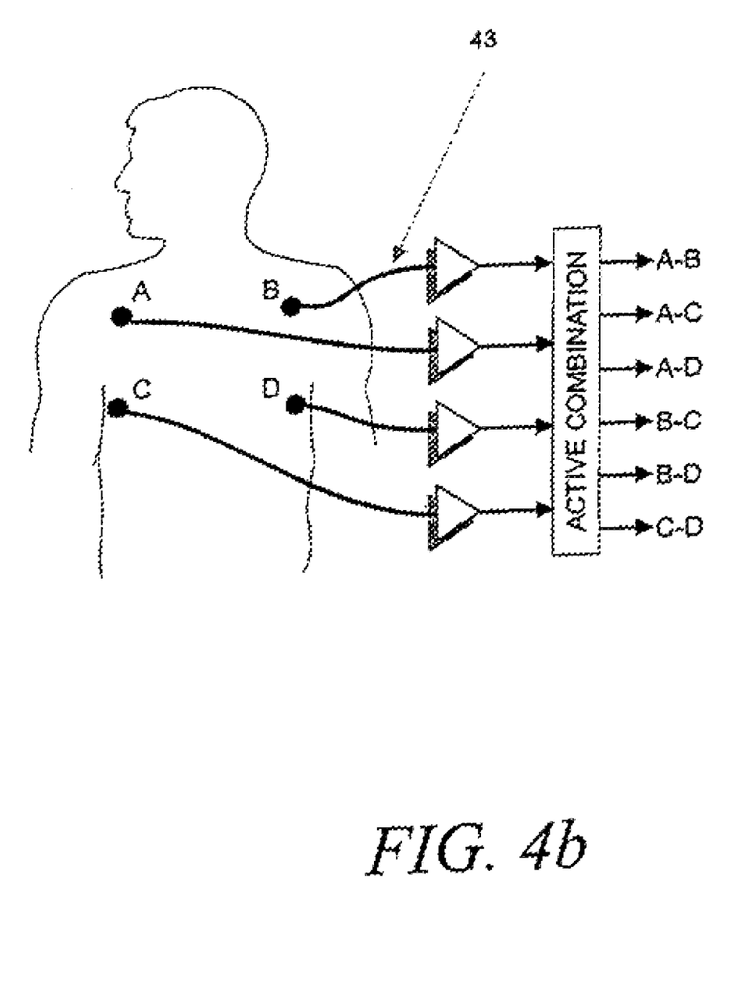
FIG. 4b illustrates a data collection interface employing "active" signal vector generation whereby signals are acquired in a unipolar manner with a common reference to the patient ground.

Referring now to FIG. 4b, there is shown a more robust data collection interface than described immediately above with reference to FIG. 4a. The data collection interface shown in FIG. 4b advantageously provides a large number of input channels with the fewest number of ECG electrodes and amplifiers. The data collection interface employs "active" signal vector generation whereby signals are acquired in a unipolar manner with a common reference to the patient ground. In other words, buffered unipolar connections are made to the ECG electrodes, such as ECG electrode 43, to enable the formation of differential ECG vector channels through a firmware combination means to provide the maximum versatility and flexibility in a small physical package.

In operation, outputs of the individual uni-polar amplifiers of the data collection interface are subtracted in appropriate combinations to form signal vectors, as is true of the differential method. One advantage of this approach is the use of fewer components to generate more effective signal vectors.

In one embodiment, 16 independent unipolar electrodes can be combined into 120 bipolar pairs (channels) providing a flexibility that is orders of magnitude higher than the previously described embodiment, as shown in FIG. 4a, based on a differential input mode configuration. The present embodiment allows for a flexible electrode montage that can be developed without undue constraints on the number of channels while, at the same time, advantageously limiting the number of electrodes to provide patient comfort and convenience and amplifiers (system weight and power).

Figure 4C:
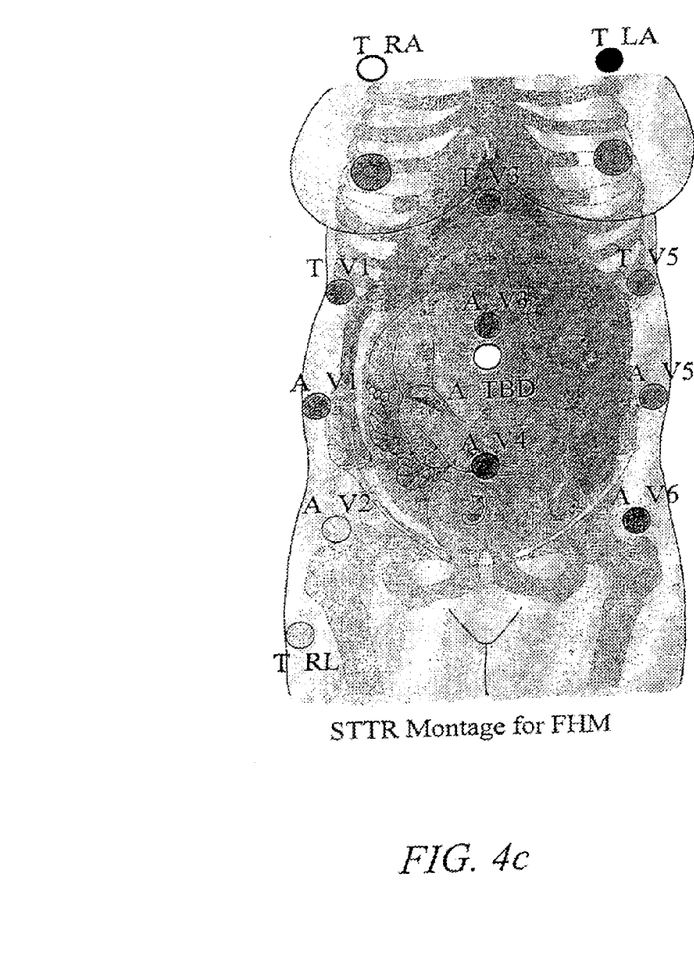
FIG. 4c is an exemplary schematic of a patient electrode montage to be interfaced to the data acquisition system described above, according to one embodiment.

FIG. 4c is an exemplary schematic of a patient electrode montage to be interfaced to the data acquisition system described above, according to one embodiment. By way of example only, the patient electrode montage uses five chest electrodes T RA, T LA, T V3, T V1, T V5, seven abdominal electrodes A V3, A V1, A V5, A V2, A V6, A V4, and a single ground reference electrode T RL.

Figure 4D:
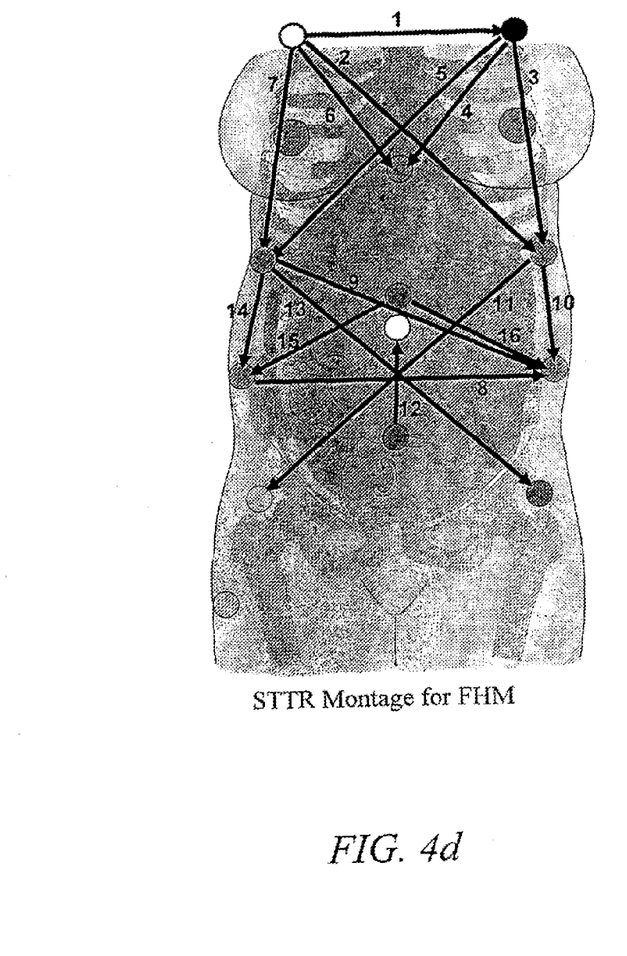
FIG. 4d illustrates the patient electrode montage of FIG. 4c comprised of sixteen differential channels (vectors)
Figure 4E:
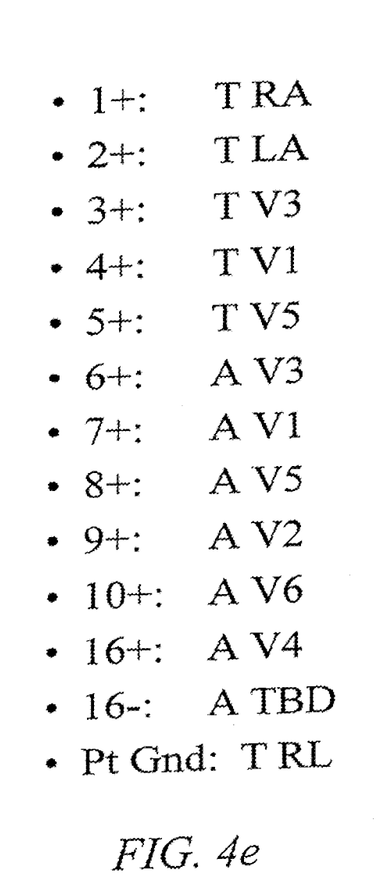
FIG. 4e illustrates the assignment of the chest and abdominal electrodes, one each per differential amplifier.
Figure 4F:
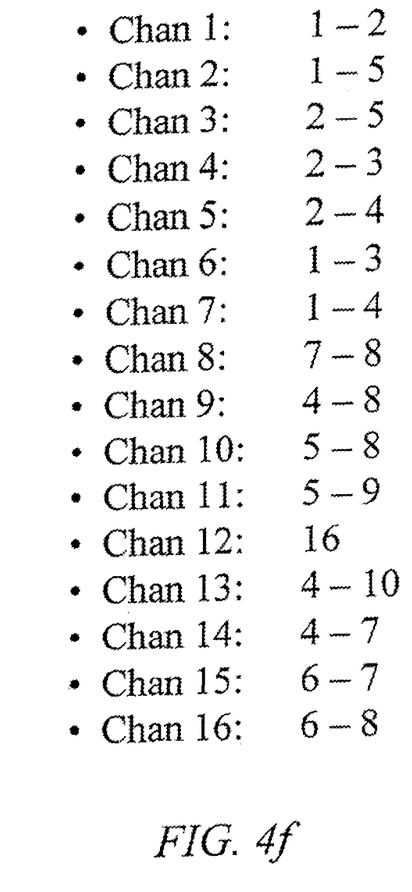
FIG. 4f illustrates the sixteen differential channels (vectors) formed by the patient electrode montage of FIG. 4d.

FIG. 4d illustrates the patient electrode montage of FIG. 4c comprised of sixteen differential channels (vectors) (See FIG. 4f) that are formed using the chest and abdominal electrodes—one each per differential amplifier (See FIG. 4e). Note that channel 12 is a dedicated differential channel that does not share any electrodes; it is the fetal reference channel. Other embodiments may utilize more or less channels. It is contemplated to utilize a sufficient number of channels to blanket the maternal abdomen with a 3-D array of measurement vectors, as shown in FIG. 4d. It should be understood that in addition to having a left-right aspect, the montage has an anterior-posterior aspect. The inventors have recognized that the fetal EKG will (nearly) align itself with at least one vector for use as a primary reference for cancellation and enhancement.

Referring again to FIG. 3, the ECG Montage 102 outputs 6 channels of data, which represents the maximum number of differential pairs for the four attached electrodes A, B, C and D, where each channel represents a differently oriented vector for collecting both a maternal only signal type and a maternal-plus-fetal signal type. It should be understood that in other embodiments the number of electrodes is greater than four, thereby producing an increased number of channels. Each channel is preferably amplified prior to being received at ECG Montage 102. The output of ECG Montage 102 is filtered 104 in order to reject noise and provide anti-aliasing for subsequent digitization.

The first phase of signal processing applies a large outlier editor 205 to the output of filter 104. The outlier editor 205 is configured to remove effects due to interference in the data stream prior to performing least-mean-square (LMS) processes on the data at the next stage, i.e. Maternal Cancellation 206.

The "outlier" effects may arise from transients from various sources which can be quite large and can, in some cases, occur over significant parts of a data set. These transients have two adverse effects on data collection. First, any data in the presence of such transients is considered corrupted and therefore unusable. Second, their presence disrupts parameter values in the adaptive cancellation process, which must then re-adapt to the signal of interest after they are no longer present.

The large outlier editor 205 operates by taking a time-series data set and removing all data that is greater than 10 standard deviations of the absolute value. These so-called "large values" and their neighboring bins (+/−150 bins) are replaced with zero values in the original data set.

At the maternal cancellation processing stage 206, a signal processing algorithm can use a least mean squares (LMS) algorithm to dynamically weigh all of the filtered vectors, output from the filtering stage 104. The maternal cancellation stage 206 is described more fully in U.S. Pat. No. 6,751,498 and the references cited therein, which are all incorporated in their entireties herein by reference.

Data output from the maternal cancellation processing stage 206 is supplied to the enhancement stage 208 and to the maternal RR detect stage 212. The maternal RR detect stage 212 refers to processing steps used to estimate the time between successive R-waves in an EKG signal. In one embodiment, data output from the maternal RR detect stage 212 is provided as input to be processed by a bandpass filter, after which, the data is compared to a threshold detector to identify the peaks of the R-waves. The time differential between successive R-wave peaks is computed and provided as an output. Data output from the maternal cancellation processing stage 206 is also supplied to the enhancement stage 208. At the enhancement stage 208, the same signal processing algorithm that was used in the maternal cancellation stage (i.e, the LMS algorithm) is used, but in this case the goal is to linearly combine the weighed signals from the maternally canceled stage in such a way that maximizes the correlated signals (the fetal EKG) and reduces any uncorrelated noise in the signals. This is using the LMS algorithm in an enhancement mode as opposed to the cancellation mode (where the goal is to remove the correlated signal, in this case the maternal EKG, from the previous stage).

As shown in FIG. 3, the filter data module 104, maternal cancellation module 206 and enhancement module 208, each interact with the long term scale monitoring module 240 as part of a feedback loop for monitoring the set of input channels (vectors) and processing parameters on a long time-scale to ensure that the final fetal ECG is optimal. In the presently described embodiment, the parameters to be monitored on a long term scale to ensure an optimal fetal ECG include: Filter Data Module 104 parameters including: (a) processing window length, (b) window overlap, (c) filter cutoffs; Maternal Cancellation Module 206 parameters including: (a) Input channel weights, (b) LMS learning coefficient, (c) Weiner Filter Length; and Enhancement Module 208 parameters including: (a) Input channel weights, (b) LMS learning coefficient, (c) Weiner Filter Length.

The feedback loop is one method for adjusting the parameters defined above to maintain their optimal setting, without operator intervention, in the context of variations such as, for example, different patient to patient ECG characteristics, or shifts in fetal position during data collection. In different embodiments, the feedback loop can be implemented using one of a number of standard techniques, which are well known. In one embodiment, the feedback loop operates by continuously monitoring an output quality metric, which is output from the Compute Data Quality Value module 218. If the score becomes unsatisfactory (i.e., the quality of the signal falls outside of acceptable limits) the system 300 enters a calibration mode in which it seeks to change the adjustable parameters so as to minimize the output quality metric score by performing a "steepest descent" search in the space spanned by the parameters. In a "steepest descent" search, the system alternates "gradient estimation" steps with "minimization steps." "Gradient estimation steps" assess the sensitivity of the output quality metric to small variations in the vector of parameters, thereby obtaining numerical estimates of the gradient of the output metric with respect to the vector of adjustable parameters, at the current system settings. "Minimization" steps numerically seek the parameter vector that minimizes the output metric by moving downward along the direction of the gradient vector.

With continued reference to FIG. 3, operation of the feedback loop comprises the "Long Term Scale Monitoring" Module 240 receiving data (i.e., "quality scores" and other optional metrics described above) output from the Compute Data Quality Value module 218. An optimization procedure, running in the "Long Term Scale Monitoring" Module 240 continuously seeks to minimize the "quality scores" and other metrics output from the Compute Data Quality Value module 218 by adjusting one or more of the following parameters:

bipolar montage combination weights (Element 102)

processing window length, window overlap, and filter cutoffs (Element 104)

input channel weights, LMS learning coefficient, and Wiener Filter length (Element 206)

input channel weights, LMS learning coefficient, and Wiener Filter length (Element 208)

Figure 5A:
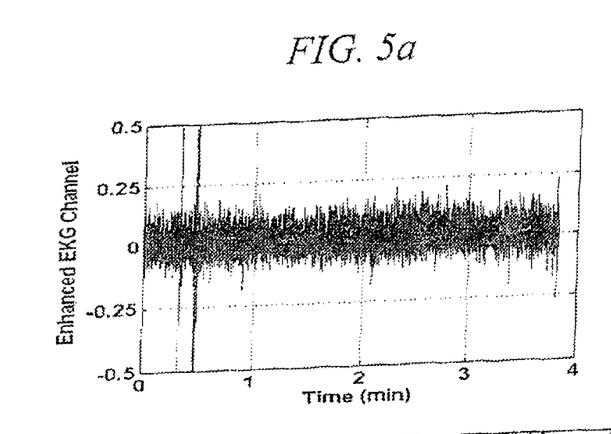
FIGS. 5a-c illustrate by way of example, the monitoring process for a "good" fetal ECG channel.
Figure 5B:
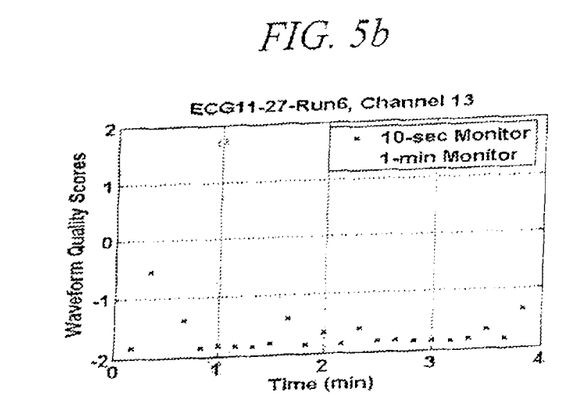
Figure 5C:
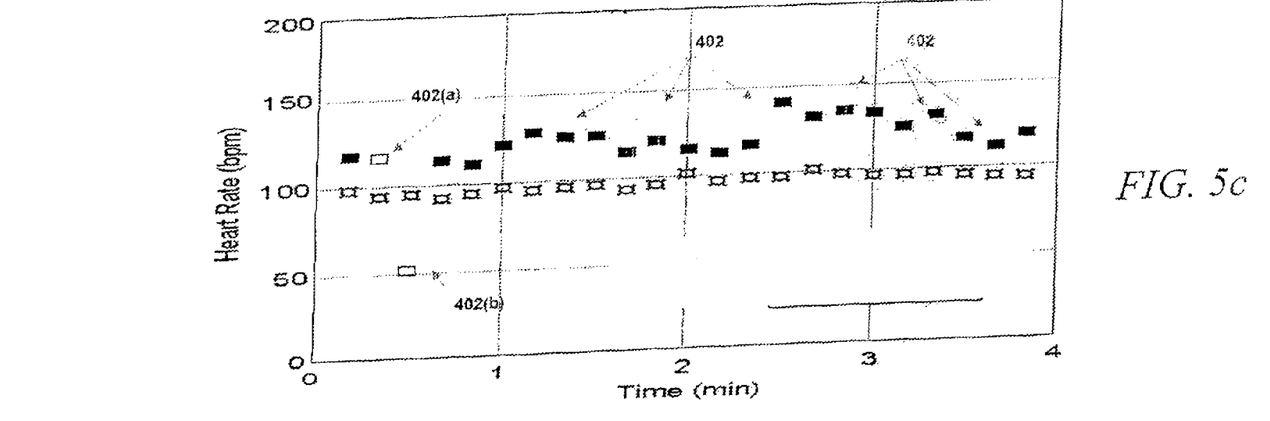

FIGS. 5*a-c* illustrate by way of example, the monitoring process for a "good" fetal ECG channel.

FIG. 5*a* is a time-series plot of the data. In particular, FIG. 5*a* illustrates a 4-minute time-series plot of the enhanced fetal ECG. The time scale of the plot is too compressed to be able to discriminate individual R-peaks. Instead it illustrates a brief segment of noisy data (first 30-seconds) followed by a period of low noise data.

FIG. 5*b* illustrates the data's waveform quality scores with large negative waveform quality values being more desirable. The waveform quality scores computed at both the short and long time-scales. The 10-second scores (annotated by 'x' markers) show the variability in the waveform's quality (scores less than −1 represent "excellent" data). In contrast, the 1-minute scores (annotated by 'square' markers) show results computed for the long time-scale period. This result monitors the overall quality of the channel being processed and will be used in the control feedback processing to evaluate whether or not the processing parameters can be updated to optimize the results.

FIG. 5*c* illustrates the computed maternal and fetal heart rates. The maternal heart rate (annotated by 'diamond' markers) is consistent throughout the 4-minutes at a value of 100 bpm. The fetal heart rate 402 (denoted by rectangle markers) shows some variability, and is color coded in the actual display such that a "good" waveform quality score is indicated in green and a "bad" waveform quality score in red. Since colors can not be shown in this document, it is noted that the second and third fetal data points (402(*a*), 402(*b*)) have low waveform quality (colored red) that is consistent with the behavior observed in FIG. 5*a*.

It should be noted that while FIGS. 5*b-c* are presented as single points for the 10-second assessment intervals, the processed fetal ECG data are time-continuous.

Figure 6A:
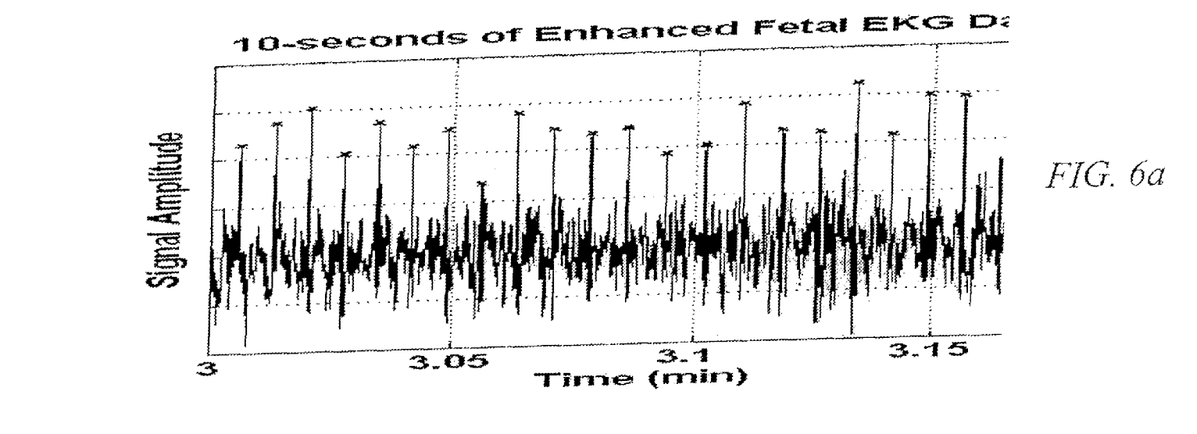
FIGS. 6a and 6b illustrate representative full-resolution time history of the processed fetal ECG.
Figure 6B:
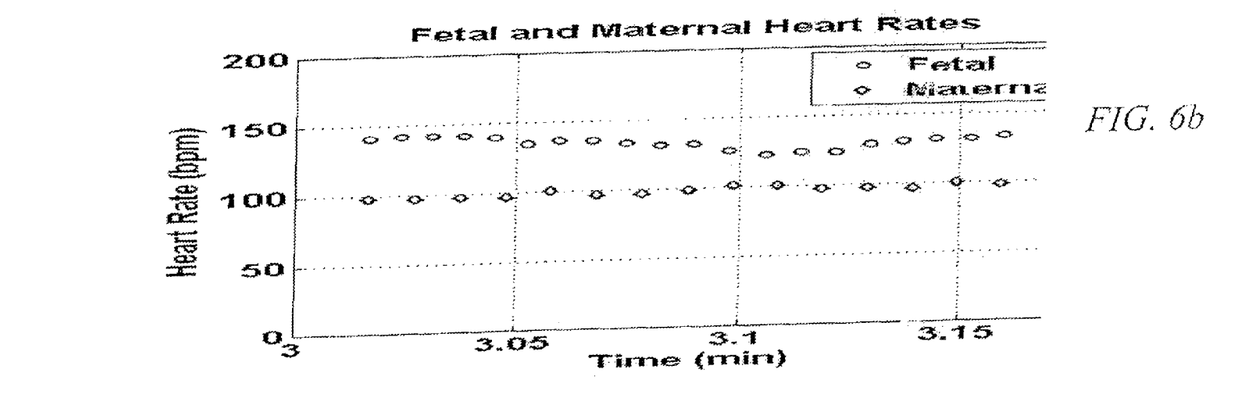

With reference now to FIGS. 6*a* and 6*b*, there is shown a representative full-resolution time history of the processed fetal ECG.

FIG. 6*a* illustrates a 10-second time history with automatically located R-peaks that begins at the third minute. The peak of each R-wave is annotated with an 'X' on FIG. 6*a*; these are the automatically detected R-peaks of the fetal ECG waveform.

FIG. 6*b* is a corresponding plot of instantaneous maternal and fetal heart rate computed from the R-to-R peak intervals. Thus, the clinician can be provided the instantaneous heart rates (plotted points) and a data quality metric, where data quality is indicated by color as in FIG. 5*c*.

As described, above, the automated monitoring focuses on a single fetal ECG channel. The long time-scale monitoring can be extended to all enhancement channels of a given ECG montage, and thus evaluate if the optimal output channel is selected.

Figure 7:
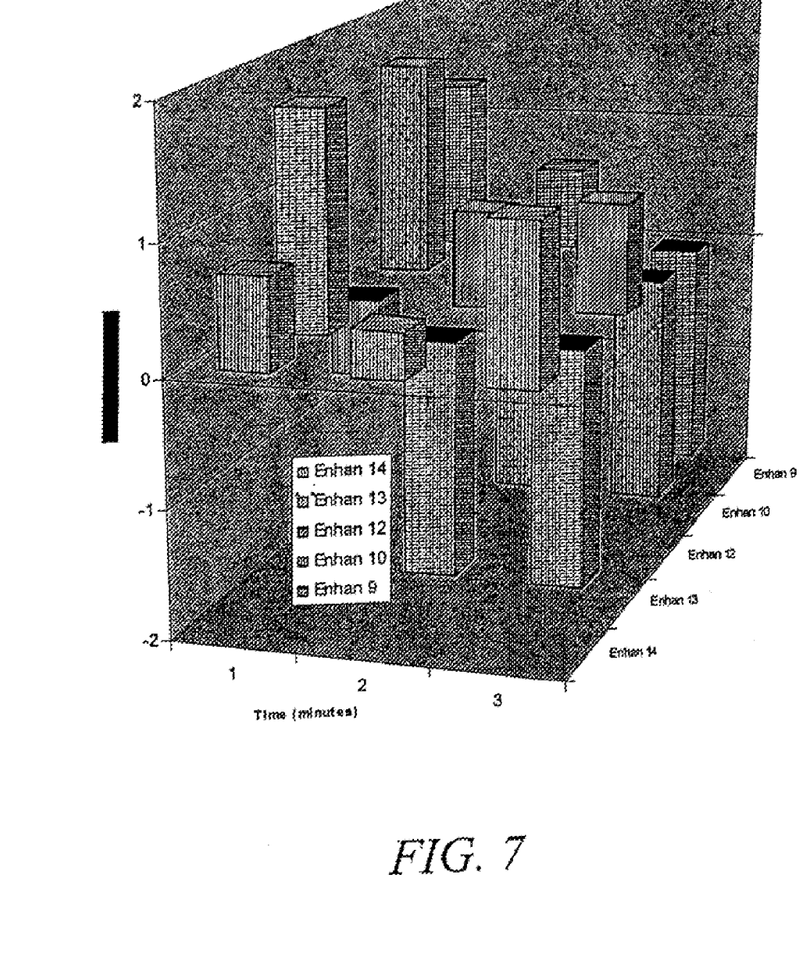
FIG. 7 illustrates the waveform quality scores for the long time-scale for nine enhancement channels of one data collection.

FIG. 7 illustrates the waveform quality scores for the long time-scale for five enhancement channels of one data collection. It should be noted that, first, there is a spread to the scores; i.e., some channels produce good results while others produce poor results. Second, the waveform quality score of a given channel can vary significantly over this 4-minute segment. For example, channel 13 starts off with the worst quality score, and by the second and third minutes it shows one of the best quality scores. This information will be used to optimize the selection of channels and processing parameters once the full control feedback mechanism is in place.

Metrics

This section describes metrics that were developed to serve as a basis for evaluating the quality of fetal waveforms extracted by the Fetal Heart Monitoring (FHM) system. Depending on a number of factors—position and orientation of fetus, background noise and interference, quality of available propagation paths for the fetal ECG signal—the quality of the signal on a FHM channel can vary substantially and unpredictably with time. At any given time it is not unusual for the majority of channels being monitored to be substandard, but it is almost always the case that at least one channel has high quality data. The automatic evaluation methods developed under this effort provide the ability to routinely isolate those channels that present useful data, and pass them on for further processing, while discarding substandard data. They also serve as the basis for the control feedback stages described above and illustrated in FIG. 3.

The waveform evaluation method has three distinct phases: R-peak detection, metric calculation, and metric clustering. The R-peak detection methods were developed as part of a different project and are based on standard methods; the metric calculations are based on characteristics of the measured ECG waveform and detected R-wave peaks, and are described in this section. An overall waveform quality score from these metrics can be computed by using cluster analysis.

Intuitively, good estimates of heart rate require ECG waveforms with well developed R-wave peaks. The interval between R-wave peaks then provides a near instantaneous estimate of heart rate. The metrics developed for assessing waveform quality therefore focus on assessing the relative strength and regularity of the peaks observed in the extracted waveform. These metrics are defined as follows:

Signal to Noise Ratio: This is a measure of R-wave amplitude. It is the mean square amplitude of detected R-wave peaks in a selected signal block divided by the mean square value of "background" samples in that same signal block. Conceptually, "background" samples are the sample values that are not "close to" a detected peak. For this calculation, points "close to" a peak were taken to be those in a region extending $W_{pk}/2$ on either side of the peak, where $W_{pk}$ was set equal to 10% of the mean of the observed peak intervals. (Note that, in spite of the name used, "background" samples are often dominated, not by noise, but by non-R-wave components of the ECG signal.)

Fraction of Outliers from the Mean: (This metric, and the next three, are all concerned with quantifying the stability of measured intervals between R-wave peaks. The intuitive rationale is that significant residual non-fetal energy in a channel will cause missed R-wave peaks, or misidentified peaks, which will, in turn, lead to peak-to-peak intervals that vary significantly about a nominal value.) This metric looks for outliers from the mean peak-to-peak interval in the data block, where an outlier is any interval whose length does not lie within 10% of the mean interval length. That is, if the $i^{th}$ interval length is $T_i$ and either $T_i<0.9T_{av}$ or $T_i>1.1T_{av}$ (where $T_{av}$ is the mean measured interval) then the $i^{th}$ interval is an outlier. The fraction of outliers from the mean is the fraction of observed interval values that are outliers.

Fraction of Outliers from the Median: This is exactly like the preceding metric except that the median of the observed interval values, rather than the mean, is used as the central point from which differences are computed. (The median is that value, in a collection of values, at which half the values lie above and half below. It is a measure of the centroid of the collection that is not sensitive, as is the mean, to the presence of occasional very large outliers.)

Normalized Standard Deviation of RR Intervals: The square root of the variance about their mean of the observed R-to-R intervals, normalized by the mean value of the intervals. That is $$\sigma_{RR} \equiv \frac{\sqrt{\frac{1}{N_{pk}} \sum_{i=1}^{N_{pk}} (T_i - T_{av})^2}}{T_{av}}$$

where $N_{pk}$ is the number of measured peak intervals, $T_i$ is the interval between the $i^{th}$ peak and the $i+1^{st}$ peak, and $T_{av}$ is the mean of the $T_i$ values.

Normalized Median Deviation of RR Intervals: This is similar to the above, except that calculations of the mean are everywhere replaced by calculations based on the median. That is $$MD_{RR} \equiv \frac{\text{median}(|T_i - T_{med}|)}{T_{med}}$$

where 'median' is the function which return the median of a set of indexed values, and $T_{med}$=median($T_i$)

Waveform Variability: This is a measure of how consistent the shape of the ECG waveform is from one cycle to the next. The data from a block of ECG data is divided into "snips" that extend from $0.1T_{av}$ before a detected peak to $0.65T_{av}$ after the peak. ($T_{av}$ is again the mean peak-to-peak interval.) By definition, these "snips' are all the same length and each nominally has a detected R-wave peak at the same relative location. We treat these as successive samples of corresponding parts of an ECG waveform and seek to quantify how much the waveform shape varies from cycle to cycle. The underlying rationale is that the shape for a healthy ECG should be relatively stable whereas noise or contamination will cause random variations from cycle to cycle. As a basic measure of variability we compute the variance for corresponding points in each snip across all snips, and average the result over the snip length. This is normalized by an estimate of the total average power in a snip, which is obtained by computing the mean square value of corresponding points across all snips and averaging the results over snip length. The ratio of mean variance to mean power is taken as the measure of waveform variability.

As defined, these metrics are all dimensionless quantities and so are not affected by absolute scaling of the input waveforms.

In addition to the above six metrics, extracted fetal ECGs are screened using a measure of acceptability: apparent heart rate. One indicator of a noisy or contaminated fetal ECG is that measured heart rates obtained from the signal have unrealistic values. We have an optional screen in the FHM processing that rejects channels for which the apparent fetal heart rate ($1/(60T_{av})$) is less than 95 beats per minute.

Example 1

Figure 8:
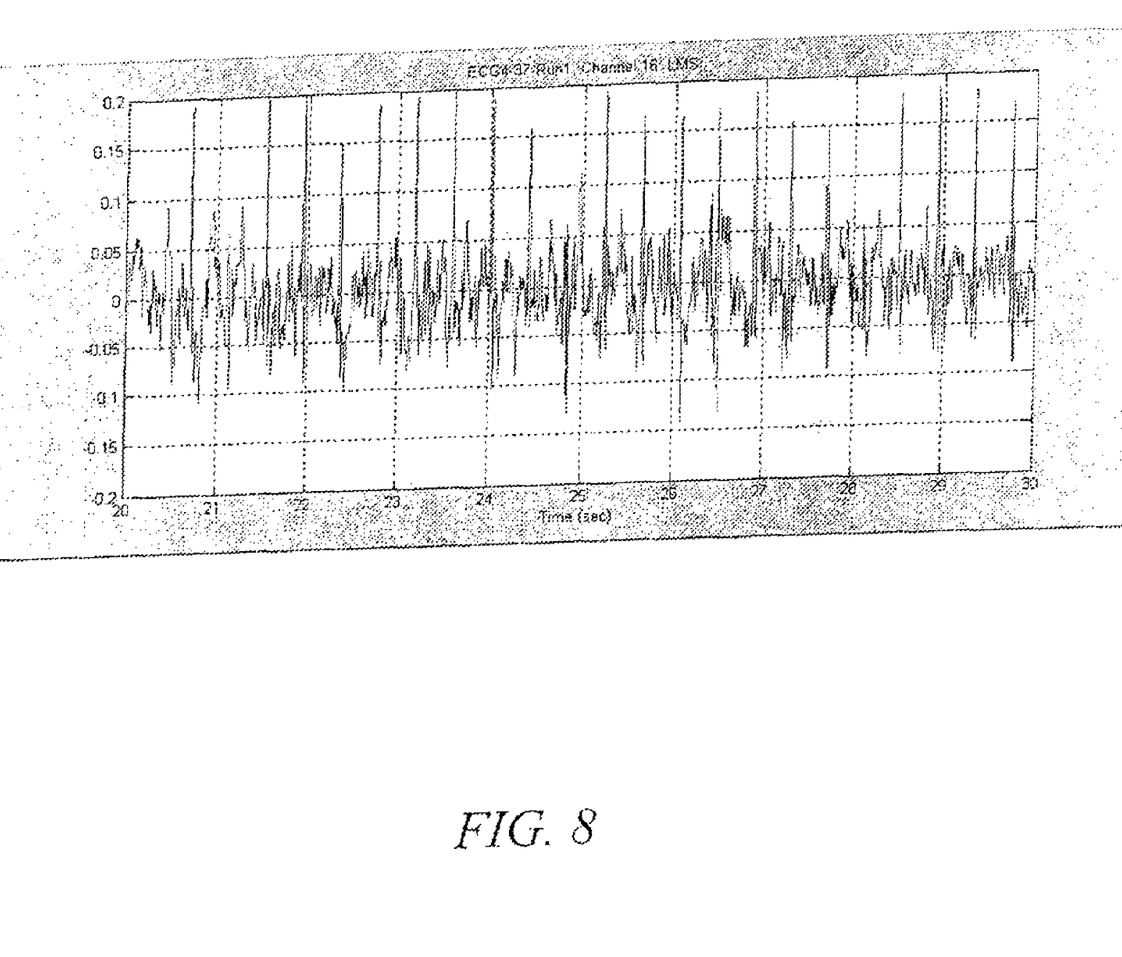
FIG. 8 is an illustration taken from a sample with well developed, regular R-wave peaks.

FIG. 8 is a first example that illustrates samples of FHM measurements; the related metric values that were computed for this sample as included as Table I, below. It is noted that FIG. 8 shows only a few seconds of waveform, while the metrics were computed from a longer segment of data—typically 30 seconds.

FIG. 8 is taken from a sample with well developed, regular R-wave peaks and illustrates typical metric values for a good data sample. For this measurement, SNR exceeds 12 (the largest values we have observed on any measurement are about 15).

Referring to Table I. below, depending on whether the mean ('foutl_mn') or the median ('foutl_med') measure is used, 18 to 25 percent of peak-to-peak intervals are tagged as outliers. (The best cases observed give around 10%; the worst 65%.) We find that the median measure of peak-to-peak variability ('fdT_med') is a somewhat better measure of peak-to-peak variability than the standard deviation ('fdT_var'). For this example it is about 5 percent. (For poor cases it is as high as 30 percent.) Finally, waveform variability ('wavef_var') is about 60 percent of mean waveform power; in poor cases it can exceed 100%.

TABLE I

| Primary Channel | SNR | foutl_mn | foutl_md | fdT_var | fdT_med | wavef_var |
| --- | --- | --- | --- | --- | --- | --- |
| ECG4-37-Run1, ch 16 | 12.55 | 0.25 | 0.18 | 0.32 | 0.05 | 0.61 |

Example 2

Figure 9:
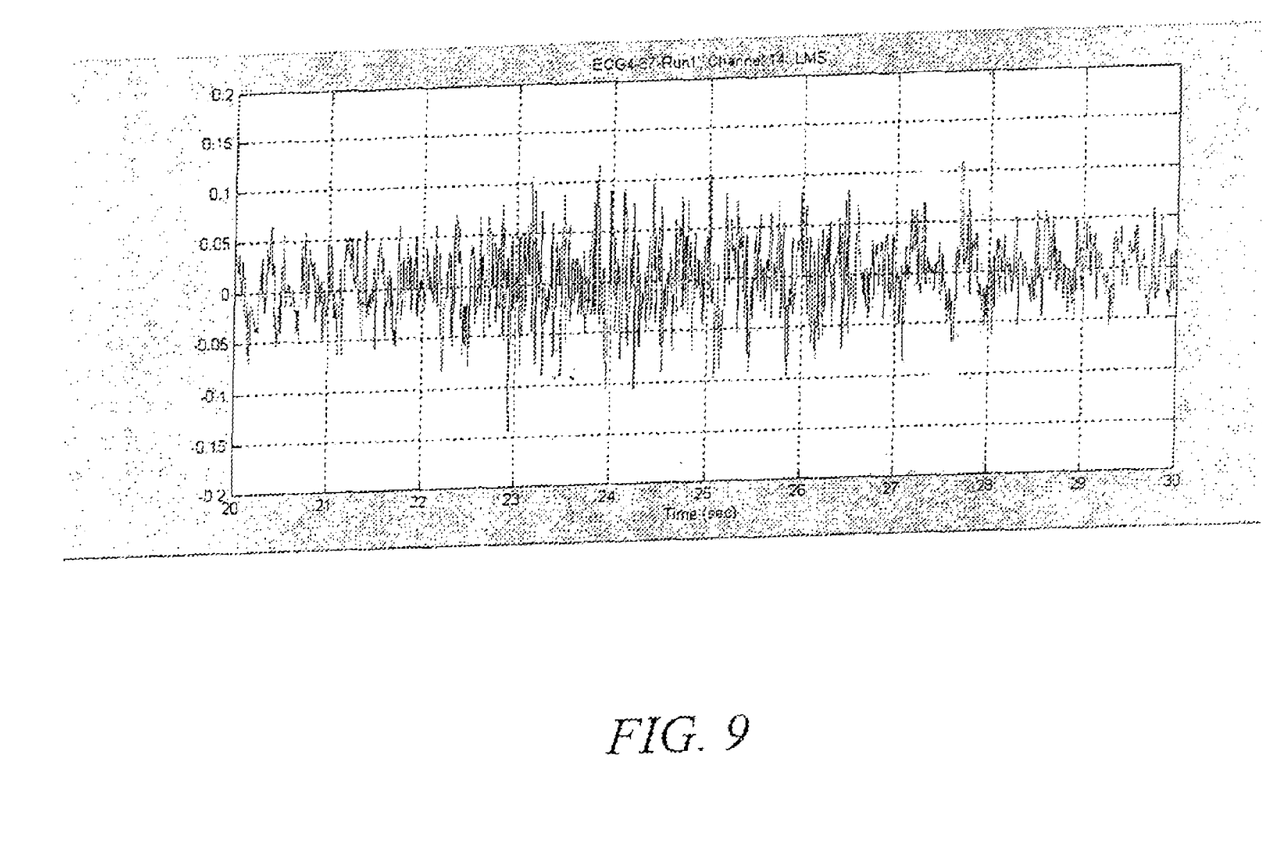
FIG. 9 is another example that illustrates samples of FHM measurements.

FIG. 9 is a second example that illustrates samples of FHM measurements; the related metric values that were computed for this sample are included as Table II. In the present example, a different channel from the same data set is used, which, as shown, tends toward the opposite extreme in quality. Referring to Table II, this example exhibits little evidence of fetal ECG energy, and the computed metric values reflect this qualitative assessment. The SNR is a little less than 5.5, over 60% of the nominal R-to-R intervals qualify as outliers, the median measure of peak-to-peak variability is 26 percent (as opposed to 5% in the first example) and waveform variability is 90 percent of mean waveform power.

TABLE II

| Primary Channel | SNR | foutl_mn | Foutl_md | FdT_var | fdT_med | wavef_var |
|---|---|---|---|---|---|---|
| ECG4-37-Run1, ch 14 | 5.42 | 0.62 | 0.63 | 0.4 | 0.26 | 0.9 |

There has thus been provided methods and systems for automated monitoring of the fetal condition in an objective, quantitative, and non-invasive manner by enabling continuous and highly specific data collection during pre-natal development and the intra-partum period. The invention automates and optimizes existing signal processing parameter controls by eliminating current requirement for certain operator decisions ("man-in-the-loop") during processing. Further, the invention provides a robust and clinically acceptable data collection interface to the patient by optimizing the data collection hardware configuration. The invention has applications in the field of fetal and maternal treatment planning, and provides regimens potentially earlier than presently feasible, thus facilitating or indicating interventions which may reduce maternal and fetal morbidity and mortality. In this regard, the health and well-being of the mother and fetus is maximized by reducing unnecessary or ineffective interventions (e.g., unnecessary C-sections) and the number of babies born with effects of such interventions.

Based on the foregoing specification, the invention may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the invention. The computer readable media may be, for instance, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network.

While the invention has been described with reference to an example embodiment, it will be understood by those skilled in the art that a variety of modifications, additions and deletions are within the scope of the invention, as defined by the following claims.

What is claimed is:

1. An automated method of monitoring the fetal electrocardiographic waveform of a fetus in a pregnant mother to extract a high quality fetal signal from an abundance of signal channels, said method comprising:
    a) measuring, in real-time, biopotential waveforms indicative of either one of a maternal heart or a maternal heart beat and a fetal heart beat;
    b) isolating a single biopotential waveform from among said measured biopotential waveforms for use as a reference fetal waveform;
    c) enhancing the isolated reference fetal waveform to remove correlated noise;
    d) monitoring the enhanced isolated reference fetal waveform in real-time via at least one fetal monitoring algorithm;
    e) monitoring an output quality metric via at least one quality metric monitoring algorithm to determine if it is within an acceptable range; and
    f) dynamically adjusting at least one processing parameter of the at least one fetal monitoring algorithm to maintain the output quality metric within said acceptable range.

2. A method according to claim 1, wherein said measuring step further comprises:
    acquiring said biopotential waveforms from at least one sensor located external to the mother;
    forming a plurality of differential electrocardiogram (ECG) bipolar vectors from the acquired biopotential waveforms.

3. A method according to claim 1, wherein said plurality of biopotential waveform signals are acquired as unipolar signals.

4. A method according to claim 1, wherein said isolating step further comprises: extracting a high quality fetal signal from an abundance of abdominal channels for use as said reference fetal waveform.

5. A method according to claim 1, wherein said enhancing step further comprises: linearly combining said measured biopotential waveforms to maximize the reference fetal waveform and reduce uncorrelated noise.

6. A method according to claim 1, wherein said monitoring step (d) further comprises: monitoring the enhanced reference fetal waveform over a short term re-evaluation interval on the order of substantially 10 to 30 seconds to determine whether the fetal heart rate is present and is within physiologically acceptable bounds.

7. A method according to claim 1, wherein said step (e) of monitoring said output quality metric further comprises: monitoring the enhanced reference fetal waveform over a long term re-evaluation interval on the order of substantially 1 to 2 minutes to determine whether a fetal heart vector has moved within a monitoring montage array.

8. A method according to claim 1, wherein said monitoring of said output quality metric further comprises:
    utilizing a quality score associated with the quality of the fetal waveform, based on one or more metrics, and
    dynamically adjusting appropriate parameters when said quality score falls below a predetermined threshold to ensure that the quality of the fetal waveform is optimized.

9. A method according to claim 4, wherein said quality metric is selected from the group consisting of: (a) outliers from the mean, (b) fraction of outliers from the median, (c) waveform variability, (d) normalized median deviation of RR intervals, (e) signal to noise ratio and (f) normalized standard deviation of RR intervals.

10. A method according to claim 1, wherein said step of dynamically adjusting said one or more processing parameters further comprises: dynamically adjusting said one or more processing parameters associated with said at least one fetal monitoring algorithm, to adjust its sensitivity, accuracy and rapidity of convergence to estimates of interest.

11. A method according to claim 1, wherein said one or more processing parameters are based on certain input data characteristics of said measured biopotential waveforms and a pre-defined set of rules.

12. A method according to claim 1, wherein said one or more processing parameters are selected from the group consisting of (a) processing window length, (b) window overlap, (c) filter cutoffs, (d) input channel weights, (e) LMS learning coefficient, (f) Weiner filter length.

13. A method according to claim 1, wherein said step of dynamically adjusting one or more processing parameters further comprises the step of: continuously minimizing quality scores.

14. A system for monitoring the fetal electrocardiographic waveform of a fetus in a pregnant mother to extract a high quality fetal signal from an abundance of abdominal channels, said system comprising:
   a) means for measuring, in real-time, biopotential waveforms indicative of either one of a maternal heart or a maternal heart beat and a fetal heart beat;
   b) means for isolating a single biopotential waveform from among said measured biopotential waveforms for use as a reference fetal waveform;
   c) means for enhancing the isolated reference fetal waveform to remove correlated noise;
   e) means for monitoring the enhanced isolated reference fetal waveform in real-time via at least one fetal monitoring algorithm;
   f) means for monitoring an output quality metric via at least one quality metric monitoring algorithm to determine if it is within an acceptable range; and
   g) means for dynamically adjusting at least one processing parameter of the at least one fetal monitoring algorithm to maintain the output quality metric within said acceptable range.

15. A system according to claim 14, wherein said means for measuring further comprises:
   means for acquiring said biopotential waveforms from at least one sensor located external to the mother; and
   means for forming a plurality of differential electrocardiogram (ECG) bipolar vectors from the acquired biopotential waveforms.

16. A system according to claim 14, wherein said plurality of biopotential waveform signals are acquired as unipolar signals.

17. A system according to claim 14, wherein said means for enhancing comprises: linearly combining said measured biopotential waveforms to maximize the reference fetal waveform and reduce uncorrelated noise.

18. A system according to claim 14, wherein said monitoring step comprises: monitoring the enhanced reference fetal waveform over a short term re-evaluation interval on the order of substantially 10 to 30 seconds to determine whether the fetal heart rate is present and is within physiologically acceptable bounds.

19. A system to claim 14, wherein said means for dynamically adjusting said one or more processing parameters further comprises: dynamically adjusting said one or more processing parameters associated with said at least one fetal monitoring algorithm, to adjust its sensitivity, accuracy and rapidity of convergence to estimates of interest.

20. A system according to claim 14, wherein said one or more processing parameters are based on certain input data characteristics of said measured biopotential waveforms and a pre-defined set of rules.

21. A system according to claim 14, wherein said one or more processing parameters are selected from the group consisting of: (a) processing window length, (b) window overlap, (c) filter cutoffs, (d) input channel weights, (e) LMS learning coefficient, (f) Weiner filter length.

22. A system according to claim 14, wherein said means for dynamically adjusting one or more processing parameters further comprises means for continuously minimizing quality scores.

* * * * *